(12) United States Patent
Murase et al.

(10) Patent No.: US 8,829,057 B2
(45) Date of Patent: Sep. 9, 2014

(54) AMPK ACTIVATING AGENT

(75) Inventors: Takatoshi Murase, Haga-gun (JP); Yoshihiko Minegishi, Haga-gun (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/008,086

(22) Filed: Jan. 18, 2011

(65) Prior Publication Data

US 2011/0118359 A1 May 19, 2011

Related U.S. Application Data

(62) Division of application No. 11/480,504, filed on Jul. 5, 2006, now abandoned.

(30) Foreign Application Priority Data

Sep. 5, 2005 (JP) ................................ 2005-257047
Nov. 24, 2005 (JP) ................................ 2005-338405

(51) Int. Cl.
*A61K 31/12* (2006.01)

(52) U.S. Cl.
USPC ........................................................ 514/691

(58) Field of Classification Search
None
See application file for complete search history.

(56) References Cited

U.S. PATENT DOCUMENTS

| | | | |
|---|---|---|---|
| 4,562,087 A | 12/1985 | Kryger | |
| 2003/0026811 A1 | 2/2003 | Hirayama et al. | |
| 2003/0039616 A1 | 2/2003 | Hanada et al. | |
| 2003/0054015 A1 | 3/2003 | Haze et al. | |
| 2003/0202946 A1 | 10/2003 | Hanada et al. | |
| 2005/0003976 A1 | 1/2005 | Haze et al. | |
| 2005/0084548 A1 | 4/2005 | Tsuda et al. | |
| 2005/0158264 A1 | 7/2005 | Haze et al. | |
| 2005/0175764 A1 | 8/2005 | Takagaki | |
| 2007/0244202 A1 | 10/2007 | Murase | |
| 2008/0102043 A1 | 5/2008 | Hanada et al. | |
| 2008/0125496 A1 | 5/2008 | Hanada et al. | |

FOREIGN PATENT DOCUMENTS

| | | | |
|---|---|---|---|
| EP | 1 671 963 A1 | 6/2006 | |
| JP | 5-123135 | 5/1993 | |
| JP | 8-47381 | 2/1996 | |
| JP | 2002-186424 | 7/2002 | |
| JP | 2002-193824 | 7/2002 | |
| JP | 2002-265978 | 9/2002 | |
| JP | 2003-104879 | 4/2003 | |
| JP | 2003-137803 | 5/2003 | |
| JP | 2003-252766 | 9/2003 | |
| JP | 2003-261445 | 9/2003 | |
| JP | 2003-286180 | 10/2003 | |
| JP | 2003-334022 | 11/2003 | |
| JP | 2005-47935 | 2/2005 | |
| JP | 2005-89384 | 4/2005 | |
| JP | 2005-97161 | 4/2005 | |
| JP | 2005-97162 | 4/2005 | |
| JP | 2005-137204 | 6/2005 | |
| JP | 2005272401 | 6/2005 | |
| JP | 2005-194252 | 7/2005 | |
| JP | 2005-198642 | 7/2005 | |
| JP | 2006-272401 | * 10/2005 | ............. A61K 33/08 |

OTHER PUBLICATIONS

Derwent Summary, Accession No. 2005-670729.*
Burfield (Grapefruit Oil Supply Situation and Grapefruit Juice Contraindications, 2005).*
www.clearwayhealth.com (accessed Jan. 12, 2012).*
Yasuhiko Minokoshi, et al., "AMP-Activated Protein Kinase and Energy Metabolism", Molecular Medicine, vol. 39, No. 4, 2002, pp. 398-407, (with partial English translation).
Yasuhiko Minokoshi, et al., "Leptin Stimulates Fatty-Acid Oxidation by Activating AMP-Activated Protein Kinase" Nature, vol. 415, Jan. 17, 2002, pp. 339-343.
Gaochao Zhou, et al., "Role of AMP-Activated Protein Kinase in Mechanism of Metformin Action", The Journal of Clinical Investigation, vol. 108, No. 8, Oct. 2001, pp. 1167-1174.
Latest Encyclopedia of Perfume and Flavor edited by Soichi Arai, 1st ed., Asakura Publishing, May 10, 2000, pp. 113, 254, (with partial English translation).
Toshimasa Yamauchi, et al., "Cloning of Adiponectin Receptors that Mediate Antidiabetic Metabolic Effects", Nature, vol. 423, Jun. 12, 2003, pp. 762-769.
Derwent Accession No. 2003-821725.
Sinclair (The Grapefruit: Its Composition, Physiology, and Products, pp. 251-267, 1972).
Fujioka et al. (Diabetes 53(Suppl 2):A594, 2004).
Office Action issued on Jan. 5, 2011, in Japanese Patent Application No. 2005-257047 (with English translation).
Office Action issued on Jan. 5, 2011, in Japanese Patent Application No. 2005-338405 (with English translation).
Constipation Causes Fatigue, www.clearwayhealth.com/constipation-fatigue.html, Mar. 8, 2012.

* cited by examiner

*Primary Examiner* — Craig Ricci

(74) *Attorney, Agent, or Firm* — Oblon, Spivak, McClelland, Maier & Neustadt, L.L.P.

(57) ABSTRACT

A method for enhancing endurance and/or for removing fatigue by administering to a subject in need thereof a composition containing an effective amount of nootkatone. The method may be further combined with exercise.

22 Claims, No Drawings

AMPK ACTIVATING AGENT

CROSS-REFERENCE TO RELATED APPLICATIONS

The present application is a divisional of U.S. Ser. No. 11/480, 504, filed on Jul. 5, 2006, which claims priority to JP 2005-257047, filed on Sep. 5, 2005, and JP 2005-338405, filed on Nov. 24, 2005.

BACKGROUND OF THE INVENTION

1. Field of the Invention

The present invention relates to an AMPK (AMP-activated protein kinase) activating agent.

2. Background of the Invention

In recent years, population with obesity has increased, and so-called lifestyle-related diseases such as diabetes associated with obesity have become grave social problems. Obesity is generated as a result of energy excess in which energy intakes exceed energy consumption. Thus, the bases for prevention and improvement of obesity and diabetes developed therewith are, for example, a decrease in energy intakes by decreasing meal size or an increase in energy consumption by exercise.

However, in the modern society, lipid intakes have increased due to the westernization of eating habits, while the amount of exercise and energy consumption have decreased due to the proliferation of automobiles, and so on. As a result, so-called lifestyle-related diseases such as diabetes have been growing in number with an increase in population with obesity and become grave social problems. Exercise has widely been acknowledged to be effective for preventing and improving a variety of lifestyle-related diseases including obesity and diabetes by promoting energy metabolism. However, it is quite difficult to perform routine exercise in real life. Therefore, it is useful, if possible, to provide some method other than exercise, which has effect similar to that brought by exercise, or to effectively exploit the action of the limited exercise. Namely, the development of exercise-substituting means that exhibits effect similar to that of exercise despite that no actual exercise has been demanded.

For example, many compounds and extracts such as a soybean extract (JP-A-2003-286180), cyanidin 3-glucoside (JP-A-2003-252766), sugarcane polyphenol (JP-A-2003-137803), D-cysteinolic acid (JP-A-2003-104879), and conjugated trienoic acid-based oil and fat (JP-A-2002-186424) have heretofore been founded as substances preventing or improving obesity. However, most of their mechanisms of action on the improvement of obesity remain unknown. Moreover, their safety is not sufficiently confirmed owing to poor history of use in foods. Thus, the fact is that their usefulness is not sufficiently established.

On the other hand, as studies on energy metabolism and on mechanisms of obesity and diabetes onset have proceeded, AMPK has been shown to play a pivotal role therein (Molecular Medicine, Vol. 39, No. 4, p. 398-407, 2002). AMPK (AMP-activated protein kinase) is a ubiquitous protein in living bodies present in the muscles, liver and the like, and is known to be a protein whose activity is elevated under such circumstances that intracellular ATP levels are decreased, thereby promoting metabolism and ATP synthesis ("metabolic sensor"). Namely, AMPK is known to promote energy consumption through its activation. However, recent research has suggested that AMPK is not only regulated by intracellular energy levels but also activated by muscular activity, leptin (Nature, Vol. 415, p. 339-343, 2002), adipocyte-derived hormones such as adiponectin (Nature, Vol. 423, p. 762-769, 2003), metformin, a therapeutic drug for diabetes, (J. Clin. Invest., Vol. 108, p. 1167-1174, 2001), and so on, and acts as an intracellular mediator of fatty acid oxidation or glucose utilization promoting action induced by them. For example, AMPK is known to activate, through the control of acetyl-CoA carboxylase (ACC) activity, carnitine palmitoyl-transferase (CPT-1) that transfers long-chain fatty acid to mitochondria, thereby promoting fatty acid oxidation. Namely, CPT-1 is strongly inhibited by malonyl-CoA, an ACC product, while AMPK is considered to phosphorylate Ser79 of the ACC, thereby suppressing the ACC activity. This suggests that drugs that activate AMPK are useful for preventing and treating lifestyle-related diseases including obesity and diabetes by promoting fatty acid oxidation and increasing energy expenditures or are useful for removing lack of exercise by exerting effect similar to that of exercise.

In addition to leptin, adiponectin, and metformin described above, AICAR (5-aminoimidazole-4-carboxamide) has previously been known as a compound that activates AMPK. However, easily available raw materials with rich history of use in foods, high safety, and excellent workability were very few until now.

In recent years, reduced endurance attributed to lack of exercise has been a problem along with the rapid aging of the population, the sophistication of transportation systems, and the progression of information/communication technology. Endurance is essential to not only athletic exercise but also all routine bodily movements including working, walking, and standing. Thus, endurance is exceedingly important for living a meaningful and healthy daily life. Exercise is said to be appropriate for enhancing endurance. However, the fact is that many persons cannot make enough time for exercise due to busyness or can not do exercise due to physical problems even if they want to do so.

Possible one means for solving these problems is to routinely ingest food ingredients having endurance-enhancing or antifatigue action. For example, the present inventors have found endurance-enhancing effect provided by the consumption of catechin (JP-A-2005-89384). Additional examples of the ingredients previously reported to have endurance-enhancing effect include a hawthorn extract (JP-A-08-47381), a *Fomes japonicus* component (JP-A-05-123135), and proanthocyanidin and lycopene (JP-A-2003-334022). Moreover, examples of the ingredients having antifatigue effect include a composition containing coenzyme Q10 and carnitine (JP-A-2005-97161) and a glutamine peptide (JP-A-2005-97162).

Nootkatone is 4,4a,5,6,7,8-hexahydro-6-isopropenyl-4,4a-dimethyl-2(3H)-naphthalenone or sesquiterpene ketone, is a substance that is present in grapefruit peels and the like, and has received much attention as a flavor because of its characteristic flavor and taste of grapefruit ("Latest Encyclopedia of Perfume and Flavor" edited by Soichi Arai, 1st ed., Asakura Publishing, May 10, 2000, p. 113, p. 254). However, its physiological activity has hardly been reported so far. Regarding grapefruits, a perfume composition containing grapefruit oil (essential oil) has been reported to activate the sympathetic nervous system, thereby exhibiting antiobesity action (JP-A-2002-193824), and an external skin preparation containing grapefruit oil (JP-A-2005-47935) has also been reported. The antiobesity action of nootkatone has never been known. Moreover, the influence of nootkatone on exercise capacity including endurance or on fatigue has never been known so far.

SUMMARY OF THE INVENTION

The present invention relates to the following inventions:
(1) an AMPK activating agent containing nootkatone as an active ingredient;
(2) a lipid metabolism activating agent containing nootkatone as an active ingredient;
(3) an antiobesity agent containing nootkatone as an active ingredient;
(4) an antidiabetic agent containing nootkatone as an active ingredient;
(5) an antiarteriosclerotic agent containing nootkatone as an active ingredient;
(6) an antihyperlipidemic agent containing nootkatone as an active ingredient;
(7) an exercise-substituting agent containing nootkatone as an active ingredient;
(8) an endurance enhancing agent containing nootkatone as an active ingredient;
(9) an antifatigue agent containing nootkatone as an active ingredient;
(10) a method for activating AMPK including administering nootkatone in an effective amount;
(11) a method for preventing, treating and/or improving lifestyle-related disease, including administering nootkatone in an effective amount;
(12) a method for substituting exercise including administering nootkatone in an effective amount; and
(13) a method for enhancing endurance and/or for removing fatigue including administering nootkatone in an effective amount.

DETAILED DESCRIPTION OF THE INVENTION

The present invention relates to provision of AMPK activating agent, endurance enhancing agent, and antifatigue agent, which have rich history of use in foods, high safety, readily available, and high workability, a method of activating AMPK, and a method of preventing, treating and/or ameliorating a life-style-related disease.

The present inventors have explored natural product materials with rich history of use in foods and have consequently found that nootkatone has AMPK-activating action and is useful by its consumption in the prevention, treatment, and improvement of life-style-related disease such as obesity, hyperlipidemia, diabetes, and arteriosclerosis, in the removal of lack of exercise, and in endurance enhancement and antifatigue.

The present invention provides AMPK activating agent, endurance enhancing agent, and antifatigue agent, each of which contains nootkatone as an active agent.

The present invention provides a method of activating AMPK characterized by administering nootkatone in an effective amount, and a method of preventing, treating and/or ameliorating a life-style-related disease characterized by administering nootkatone in an effective amount.

Because a lipid metabolism activating agent, antiobesity agent, antidiabetic agent, antiarteriosclerotic agent, antihyperlipidemic agent, exercise-substituting agent, endurance enhancing agent, and antifatigue agent of the present invention induce activation of energy metabolism such as lipid metabolism and glucose metabolism and are excellent in safety, they are useful in the prevention, treatment, and/or improvement of lifestyle-related diseases such as obesity, hyperlipidemia, diabetes, and arteriosclerosis, and are useful in the removal of lack of exercise and further in endurance enhancement and/or antifatigue for broadly defined exercise including exercise, routine bodily movements, and working by exhibiting effect similar to exercise.

In the present invention, nootkatone refers to 4,4a,5,6,7,8-hexahydro-6-isopropenyl-4,4a-dimethyl-2(3H)-naphthalenone or sesquiterpene ketone. Nootkatone includes 8 types of optical isomers.

In the present invention, these isomers can be used alone or in combination. Preferably, (+)-nootkatone represented by the following structural formula (I) is used:

[Chemical Formula 1]

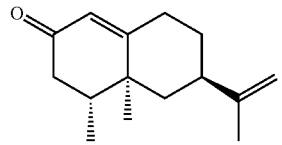

(I)

Nootkatone used in the present invention can be produced by organic chemical synthesis, synthesis with microorganisms, and the like, known in the art, and can be obtained by the methods described in, for example JP-A-2004-123561 and JP-A-2003-250591 and JP-A-1999-501052.

Alternatively, nootkatone used in the present invention can be extracted from natural products containing nootkatone by methods known in the art. In this context, the extraction can be performed by a technique appropriately combining an extraction using water, hot water, alcohol water, organic solvents, or the like, and a purification or distillation by high-performance liquid chromatography, column chromatography, or the like. Examples of the natural products containing nootkatone include grapefruits. When nootkatone is extracted from grapefruits, for example a fruit, peel, oil, concentrated juice, or squeezed juice residue of a grapefruit can be used as a raw material thereof.

Preferably, nootkatone obtained by synthesis or extraction is converted for use to a high-purity product by removing impurities by single- or multiple-step purification or the like, or may also be any semi-purified product that achieves the advantages of the present invention.

Nootkatone of the present invention has a strong AMPK-activating action in muscle cells, as shown in Examples below. Therefore, nootkatone can be used as an AMPK activating agent. The AMPK activation promotes lipid oxidation and energy consumption. Moreover, the AMPK activation increases glucose uptake via glucose transporters (GLUTs) and promotes glucose use. Thus, nootkatone is useful as a lipid metabolism activating agent, antiobesity agent, antidiabetic agent, antiarteriosclerotic agent, antihyperlipidemic agent, endurance enhancing agent, antifatigue agent, and agent for preventing, treating, and/or improving lifestyle-related disease.

Moreover, nootkatone improves a variety of symptoms partly caused by lack of exercise and is therefore useful as an exercise-substituting agent having effect similar to that of exercise. Nootkatone is useful as an exercise-substituting agent intended for the prevention and improvement of body fat accumulation, fatty liver, and lifestyle-related diseases, particularly obesity and diabetes.

In this context, the lifestyle-related diseases of the present invention refers to obesity, hyperlipidemia, diabetes, arteriosclerosis, and the like. Moreover, endurance-enhancing and antifatigue effects refer to those for broadly defined exercise including exercise, routine bodily movements, and working.

The AMPK activating agent and so on of the present invention can be administered to humans and animals and can be ingested by mixing them into a variety of foods, drinks, pharmaceuticals, pet foods, and so on.

When the agents of the present invention are used as food or drink, they can be processed as drink forms into drinks such as fruit juice drinks, carbonated drinks, tea-based drinks, dairy drinks, alcohol drinks, and soft drinks, and as food forms into foods such as jellied foods, a variety of snacks, baked goods, cake products, chocolate, gum, candy, and soups. In addition to general foods and drinks, the agents of the present invention can be applied to functional foods and drinks, invalid diets, and foods for specified health use, which present concepts of physiological function such as prevention and/or improvement of lifestyle-related diseases (e.g., obesity, hyperlipidemia, diabetes, and arteriosclerosis), enhancement of physiological function (e.g., hyperglycemia, insulin resistance, and lipid metabolism promotion) and endurance, and prevention or improvement of fatigue.

When the agents of the present invention are used as pharmaceutical drugs, they can be made into oral solid preparations such as tablets and granules and into oral liquid preparations such as internal-use liquid medicines and syrups.

When the oral solid preparations are prepared, nootkatone of the present invention can be supplemented appropriately with pharmaceutically acceptable carriers, for example excipients, if necessary, binders, disintegrants, lubricants, coloring agents, flavoring agents, and odor-improving agents, to produce tablets, coated tablets, granules, powders, capsules, and so on by routine methods. When the oral liquid preparations are prepared, nootkatone of the present invention can be supplemented with flavoring agents, buffers, stabilizers, and so on to produce internal-use liquid medicines, syrups, elixirs, and so on by routine methods.

The amount of nootkatone mixed into the food, drink, pharmaceutical drug, pet food, and so on differs depending on its usage pattern and is usually 0.0002 to 5% by mass, preferably 0.001 to 3% by mass, more preferably 0.02 to 2% by mass when nootkatone is used in the foods, drinks, and pet foods. The amount of nootkatone used in a pharmaceutical drug, for example an oral solid preparation such as tablets, granules, capsules or an oral liquid preparation such as internal-use liquid medicines and syrups is usually 0.01 to 95% by mass, preferably 0.1 to 95% by mass, more preferably 2 to 80% by mass.

The doses (effective intakes) of the AMPK activating agent, lipid metabolism activating agent, antiobesity agent, antidiabetic agent, antiarteriosclerotic agent, antihyperlipidemic agent, and exercise-substituting agent of the present invention are preferably 1 to 2000 mg/60 kg of body weight per day, more preferably 1 to 1000 mg/60 kg of body weight per day, even more preferably 2 to 1000 mg/60 kg of body weight per day, still even more preferably 2 to 700 mg/60 kg of body weight per day, yet still more preferably 5 to 500 mg/60 kg of body weight per day, in terms of the amount of nootkatone.

EXAMPLES

Example 1

A muscle cell line (C2C12) was used to evaluate the AMPK-activating action of nootkatone according to the procedures below with AMPKα and AMPKβ phosphorylation as indexes.

Cells of the murine muscle cell line (C2C12) were seeded onto a 25 cm² flask and cultured in DMEM (+10% FBS, +antimicrobial agent) at 37° C. for 1 to 2 days. When the cells became confluent, the culture solution was removed, and the cells were washed with PBS (−) and further cultured for 7 to 8 days in fresh DMEM (2% (V/V) horse serum), which was in turn replaced by a fresh culture solution every 2 to 3 days. The culture solution was then removed, and the cells were washed with PBS (−) and further cultured in fresh DMEM (−FBS) for 1 day. After the removal of the culture solution, the cells were cultured in DMEM (−FBS) containing a predetermined concentration of nootkatone (obtained from Wako Pure Chemical Industries, Ltd.) for 60 minutes. After the culture solution was subsequently removed and the cells were washed with PBS (−), 200 μL of cell lysis solution (10 mmol/L Tris (pH 7.4), 50 mmol/L sodium chloride, 30 mmol/L sodium pyrophosphate, 0.5% (V/V) Triton X-100, protease inhibitor cocktail (SIGMA P2714), phosphatase inhibitor cocktail-1 (SIGMA P2850), phosphatase inhibitor cocktail-2 (SIGMA P5726)) was added and the cell lysis solution was collected with a cell scraper. The collected cell lysis solution was well homogenized by passing it through a syringe with a 23G needle three times and then left on ice for 30 minutes. The homogenate was centrifuged at 15000 r/min at 4° C. for 15 minutes, and the resulting supernatant protein was used in the measurement below.

The concentration of the supernatant protein was measured, and the protein concentrations were then adjusted among samples to constant concentrations. To each of the samples, SDS buffer (250 mmol/L Tris, 12.5% by mass of SDS, 20% by mass of glycerin) in a ¼ volume thereof and further 2-mercaptoethanol and bromophenol blue were added. The resulting mixtures were thermally denatured at 95° C. and rapidly cooled at 4° C. to prepare samples for electrophoresis.

Predetermined amounts (approximately 20 to 40 μg) of the samples for electrophoresis were subjected to SDS-PAGE (12% gel) and transferred to a membrane. Then, phospho-AMPKα and phospho-AMPKβ were detected by using anti-phospho-AMPKα (Thr72) antibodies (manufactured by Cell Signaling Technology, Inc.) or anti-phospho-AMPKβ (Ser108) antibodies (manufactured by Cell Signaling Technology, Inc.) as primary antibodies, anti-rabbit-HRP antibodies (manufactured by Amersham Biosciences) as secondary antibodies, and Phototope-HRP Western Detection System (manufactured by Cell Signaling Technology, Inc.) as a detection reagent. The degree of AMPK activation was indicated as a relative value to that of a control (sample-free group) defined as 100 by digitizing (pixelizing) detected band strength by image analysis (EDAS290 image analysis system; KODAK).

TABLE 1

| | | Nootkatone (μmol/L) | | |
| --- | --- | --- | --- | --- |
| | Control | 50 | 100 | 150 |
| Phospho-AMPKα | 100 | 402 | 952 | 1077 |
| Phospho-AMPKβ | 100 | 241 | 314 | 358 |

As can be seen from Table 1, nootkatone has a strong AMPK-activating action in the muscle cells.

Example 2

Effect of Nootkatone

The antiobesity, antidiabetic, and antilifestyle-related disease effects of nootkatone were evaluated as described below.

Seven-week-old C57BL/6 male mice were divided into 3 groups each containing 10 mice and raised with each diet of the composition described in Table 2.

TABLE 2

| (%) | Group 1 | Group 2 | Group 3 |
| --- | --- | --- | --- |
| Plant oil | 5 | 25 | 25 |
| Lard | 0 | 5 | 5 |
| Sucrose | 0 | 13 | 13 |
| Casein | 20 | 20 | 20 |
| Potato starch | 66.5 | 28.5 | 28 |
| Vitamin | 1 | 1 | 1 |
| Mineral | 3.5 | 3.5 | 3.5 |
| Cellulose | 4 | 4 | 4 |
| Nootkatone | 0 | 0 | 0.5 |

Twenty-two weeks later, their body weights were measured, while blood was collected from the mice under ether anesthesia and under non-fasting conditions to measure serum glucose, cholesterol, triglyceride, insulin, and leptin levels. The amount of visceral fat (epididymal fat, retroperitoneal fat, and perirenal fat) was also measured. The result is shown in Table 3.

TABLE 3

| | Group 1 | Group 2 | Group 3 |
| --- | --- | --- | --- |
| Body weight (g) | 33.2 | 40.3 | 30.4 |
| Epididymal fat (g) | 0.89 | 1.91 | 0.47 |
| Retroperitoneal fat (g) | 0.27 | 0.55 | 0.15 |
| Perirenal fat (g) | 0.15 | 0.38 | 0.07 |

A remarkable rise in body weight and an increase in the amount of visceral fat were observed in Group 2 as compared with Group 1, whereas an increment of body weights and the amount of visceral fat were remarkably reduced in Group 3 as compared with Group 2. Namely, nootkatone of the present invention was shown to have excellent antiobesity effect. The result of blood analysis is shown in Table 4.

TABLE 4

| | Group 1 | Group 2 | Group 3 |
| --- | --- | --- | --- |
| Total cholesterol (mg/dL) | 137.9 | 169.4 | 131.3 |
| Triglyceride (mg/dL) | 70.9 | 95.7 | 54.3 |
| Glucose (mg/dL) | 214.1 | 240.6 | 212.3 |
| Leptin (ng/mL) | 16.6 | 33.3 | 6.2 |
| Insulin (ng/mL) | 2.56 | 3.87 | 1.26 |

A remarkable rise in blood-sugar level (glucose) was observed in Group 2 as compared with Group 1, whereas a rise in blood-glucose level was not observed in Group 3 as compared with Group 1. The blood-glucose level was also low in Group 2. Nootkatone of the present invention had excellent inhibitory effect on a rise in blood-glucose level and was therefore considered to be effective for controlling diabetes.

A remarkable rise in cholesterol level was observed in Group 2 as compared with Group 1, whereas a rise in the cholesterol level was low in Group 3 as compared with Group 1. The cholesterol level was also low in Group 2. Nootkatone of the present invention had excellent inhibitory effect on a rise in blood cholesterol level and was therefore considered to be effective for inhibiting arteriosclerosis.

A remarkable rise in triglyceride level was observed in Group 2 as compared with Group 1, whereas a rise in the triglyceride level was low in Group 3 as compared with Group 1. The triglyceride level was also low in Group 2. Nootkatone of the present invention had excellent inhibitory effect on a rise in blood triglyceride level and was therefore considered to be effective for controlling hyperlipidemia.

A remarkable rise in insulin level was observed in Group 2 as compared with Group 1, whereas a rise in the insulin level was low in Group 3 as compared with Group 1. The insulin level was also low in Group 2. Nootkatone of the present invention had excellent inhibitory effect on a rise in blood insulin level and was therefore considered to be effective for controlling hyperinsulinemia. Moreover, this result shows that nootkatone inhibits the onset of Type 2 diabetes with insulin resistance.

A remarkable rise in leptin level was observed in Group 2 as compared with Group 1, whereas a rise in leptin level was low in Group 3 as compared with Group 1. The leptin level was also low in Group 2. Nootkatone of the present invention had excellent inhibitory effect on a rise in blood leptin level and was therefore considered to be effective for controlling hyperleptinemia.

Example 3

Lipid Metabolism-Activating Effect

Seven-week-old Balb/c male mice were divided into 2 groups, to which a physiological saline (control) or nootkatone at 200 mg/kg of body weight was then orally administered for 10 consecutive days. Then, their livers and skeletal muscles (gastrocnemius muscle+soleus muscle) were collected. The livers and skeletal muscles were respectively homogenized in a buffer (250 mM sucrose, 1 mM EDTA in 10 mM HEPES (pH 7.2)), and the insoluble tissue residues were removed by centrifugation to obtain supernatants. The obtained supernatants were measured for protein levels. The protein levels were adjusted among samples to constant levels, and the samples were used in the measurement of lipid metabolism activity ($\beta$-oxidation activity). A 100-1 µg aliquot of the supernatant protein was reacted at 37° C. for 20 minutes with 0.1µ Ci [$^{14}$C]-palmitic acid in a buffer (50 mM Tris-HCl (pH 8.0), 40 mM NaCl, 2 mM KCl, 2 mM MgCl$_2$, 1 mM DTT, 5 mM ATP, 0.2 mM L-carnitine, 0.2 mM NAD, 0.06 mM FAD, 0.12 mM CoA, 3 mM $\alpha$-cyclodextrin) at the final volume of 200 µL. The reaction was terminated with 200 µL of 0.6N perchloric acid, and the unreacted [$^{14}$C]-palmitic acid palmitic acid was removed 3 times with 1 mL hexane. Lipid-degrading activity was measured by measuring radioactivity of the aqueous layer.

The measurement result is shown in Table 5. The degree of the lipid-degrading activity was indicated as a relative value to that of the control defined as 100. The lipid-degrading activity ($\beta$-oxidation activity) of the liver and skeletal muscle remarkably increased in the mice fed with nootkatone. Thus, nootkatone was shown to be effective for activating lipid metabolism. Nootkatone also improved a variety of the symptoms partly caused by lack of exercise via its AMPK-activating action and was therefore shown to be useful as an exercise-substituting agent having effect similar to that of exercise, particularly an exercise-substituting agent intended for the prevention and improvement of obesity, body fat accumulation, diabetes, fatty liver, lifestyle-related disease, and the like.

TABLE 5

|  | Control | Nootkatone |
| --- | --- | --- |
| Liver | 100 | 273 |
| Skeletal muscle | 100 | 271 |

Example 4

Evaluation of Endurance-Enhancing and Antifatigue Effects of Nootkatone

The endurance-enhancing and antifatigue effects of nootkatone were evaluated as described below. Nootkatone used was a product of Avocado.

The endurance-enhancing and antifatigue effects were evaluated according to the measurement method of maximum swimming time of mice (Reference: Am J Physiol Regul Integr Comp Physiol, Vol. 288, R708-R715, 2005) in a current water pool. The experimental pool used was a clear acrylic pool (90 cm long×45 cm wide×45 cm deep) filled to a depth of 38 cm with water maintained at 34° C. with a heater. The current in the pool was generated with a pump (C-P60H, manufactured by Hitachi), and the current speed was adjusted by connecting Water flowmeter (Tofco) to the pump and opening and closing a valve. The current speed was measured with a digital current meter (SV-101-25S, Sankou Seimitsu Kogyo).

Experimental animals used were 5-week-old Balb/c male mice (Charles River Laboratories, Inc.). The mice were preliminarily raised for 1 week under a constant raising environment (23±2° C., light period: 7 a.m. to 7 p.m.) and acclimated. In subsequent 1-week training, the mice were accustomed to swimming exercise three times a week (subjected to swimming exercise for 30 minutes at a current speed of 5 L/min on the first day, and for 30 minutes at a current speed of 6 L/min on the third and fifth days). For the next one week, the maximum swimming time of each of the individuals fasted for 2 hours was measured twice at a current speed of 7 L/min (maximum swimming time was set to the point in time when the mouse failed to rise to the surface of the water to breathe and was rescued). The mice were divided into 2 groups, a test diet group and a control diet group, each containing 8 mice, to prevent a difference in maximum swimming time between the groups. Diets prepared in the formulation composition shown in Table 8 were used to raise the mice for 10 weeks. During this period, the measurement of maximum swimming time (7 L/min) and training (6 L/min, 30 minutes) were performed once every week. The maximum swimming times of the mice on the 10th week of raising are shown in Table 7.

TABLE 6

Composition of diet (% by mass)

|  | Control diet | Test diet |
| --- | --- | --- |
| Lipid (%) | 10 | 10 |
| Casein (%) | 20 | 20 |
| Potato starch (%) | 55.5 | 55.3 |
| Cellulose (%) | 8.1 | 8.1 |
| Vitamin (%) | 2.2 | 2.2 |
| Methionine (%) | 0.2 | 0.2 |
| Mineral (%) | 4 | 4 |
| Nootkatone (%) | 0 | 0.2 |
| Total (%) | 100 | 100 |

TABLE 7

Maximum swimming time before and after 10-week raising

|  | Before raising | | After 10 week | |
| --- | --- | --- | --- | --- |
|  | Maximum swimming time (min) | Statistically significant difference | Maximum swimming time (min) | Statistically significant difference |
| Control diet | 27.32 ± 1.39 |  | 31.08 ± 2.34 |  |
| Test diet | 27.31 ± 1.72 | N.S | 40.01 ± 3.17 | P < 0.05 |

* Statistically significant difference is relative to the control group (t-test)

As can be seen from Table 7, the maximum swimming time after 10-week raising is significantly prolonged in the mice fed with the test diet containing nootkatone as compared with the control diet group, and nootkatone has endurance-enhancing and antifatigue effects.

Example 5

Preparation Examples

A variety of preparations described in (1) to (21) below were manufactured.

(1) Capsule for Prevention or Improvement of Lifestyle-Related Diseases

Compositions (300 mg) described below were encapsulated into an encapsulating agent.

TABLE 8

| Nootkatone | 50% by weight |
| --- | --- |
| Corn starch | 20 |
| Cellulose | 18 |
| Tocopherol | 2 |
| Lactose | 10 |

(2) Tablet for Prevention or Improvement of Lifestyle-Related Diseases

Compositions (1 tablet=250 mg) described below were tableted to produce a tablet.

TABLE 9

| Nootkatone | 20% by weight |
| --- | --- |
| Corn starch | 20 |
| Cellulose | 20 |
| Vitamin C | 20 |
| Lactose | 20 |

(3) Granule for Prevention or Improvement of Lifestyle-Related Diseases

Compositions (1 bag=500 mg) described below were mixed to produce a granule.

TABLE 10

| Nootkatone | 25% by weight |
| --- | --- |
| Fructose | 30 |
| Glucose | 30 |
| Skimmed milk powder | 10 |
| Caffeine | 5 |

(4) Drink for Prevention or Improvement of Obesity or Lifestyle-Related Disease

Compositions described below were mixed to produce a fruit juice drink.

TABLE 11

| | |
|---|---|
| Nootkatone | 100 mg |
| Grapefruit juice | 500 mL |

(5) Drink for Prevention or Improvement of Obesity or Lifestyle-Related Disease

Compositions described below were mixed to produce a fruit juice drink.

TABLE 12

| | |
|---|---|
| Nootkatone | 50 mg |
| Vitamin C | 300 mg |
| Orange juice | 300 mL |
| Water | 200 mL |
| Flavor | Certain quantity |
| Isomerized sugar | 5 g |

(6) Drink for Prevention or Improvement of Obesity or Lifestyle-Related Disease

Compositions described below were mixed to produce a tea drink.

TABLE 13

| | |
|---|---|
| Nootkatone | 20 mg |
| Tea catechin | 200 mg |
| Vitamin C | 500 mg |
| Green tea | 500 mL |

(7) Drink for Prevention or Improvement of Obesity or Lifestyle-Related Disease

Compositions described below were mixed to produce a sports drink.

TABLE 14

| | |
|---|---|
| Water | 500 mL |
| Nootkatone | 60 mg |
| Fructose | 3 g |
| Glucose | 2 g |
| Vitamin C | 500 mg |
| Citric acid | 100 mg |
| Sodium citrate | 2 g |
| Flavor | Certain quantity |
| Malic acid | 200 mg |

(8) Exercise-Substituting Functional Drink

A carbonated drink of the composition below was produced.

TABLE 15

| | |
|---|---|
| Nootkatone | 50 mg |
| Vitamin C | 500 mg |
| Carbonated water | 495 mL |
| Lemon juice | 5 mL |
| Flavor | Certain quantity |
| Aspartame | 5 g |

(9) Exercise-Substituting Functional Drink

A carbonated drink of the composition below was produced.

TABLE 16

| | |
|---|---|
| Nootkatone | 100 mg |
| Vitamin C | 500 mg |
| Carbonated water | 500 mL |
| Lemon juice | 5 mL |

TABLE 16-continued

| | |
|---|---|
| Flavor | Certain quantity |
| Aspartame | 5 g |

(10) Exercise-Substituting Functional Food

Compositions (1 tablet=1000 mg) described below were tableted to produce a chewable tablet food.

TABLE 17

| | |
|---|---|
| Nootkatone | 2.5% by mass |
| Maltose | 11 |
| Lactose | 30 |
| Glucose | 15 |
| Vitamin C | 20 |
| Vitamin E | 1 |
| Cellulose | 10 |
| Xylitol | 10 |
| Flavor | 0.5 |

(11) Exercise-Substituting Functional Drink

A carbonated drink of the composition below was produced.

TABLE 18

| | |
|---|---|
| Nootkatone | 10 mg |
| Vitamin C | 500 mg |
| Carbonated water | 500 mL |
| Lemon juice | 5 mL |
| Flavor | Certain quantity |
| Aspartame | 5 g |

(12) Drink for Prevention or Improvement of Obesity or Lifestyle-Related Diseases Compositions described below were mixed to produce a drink.

TABLE 19

| | |
|---|---|
| Water | 350 mL |
| Nootkatone | 5 mg |
| Fructose | 3 g |
| Glucose | 2 g |
| Vitamin C | 750 mg |
| Citric acid | 100 mg |
| Sodium citrate | 1.5 g |
| Flavor | Certain quantity |
| Malic acid | 150 mg |

(13) Drink for Prevention or Improvement of Obesity or Lifestyle-Related Diseases Compositions described below were mixed to produce a fruit juice drink.

TABLE 20

| | |
|---|---|
| Nootkatone | 4 mg |
| Vitamin C | 300 mg |
| Orange juice | 300 mL |
| Water | 200 mL |
| Flavor | Certain quantity |
| Isomerized sugar | 5 g |

(14) Tablet for Prevention or Improvement of Lifestyle-Related Diseases

Compositions (1 tablet=250 mg) described below were tableted to produce a tablet.

TABLE 21

| Nootkatone | 5% by weight |
|---|---|
| Corn starch | 35 |
| Cellulose | 20 |
| Vitamin C | 20 |
| Lactose | 20 |

(15) Drink for Endurance Enhancement or Antifatigue

Compositions described below were mixed to produce a fruit juice drink.

TABLE 22

| Nootkatone | 5 mg |
|---|---|
| Vitamin C | 300 mg |
| Grapefruit juice | 400 mL |
| Water | 100 mL |
| Flavor | Certain quantity |
| Glucose | 2 g |

(16) Capsule for Endurance Enhancement or Antifatigue

Compositions (300 mg) described below were encapsulated into an encapsulating agent.

TABLE 23

| Nootkatone | 5% by mass |
|---|---|
| Vitamin C | 20 |
| Cellulose | 10 |
| Corn starch | 40 |
| Tocopherol | 2 |
| Lactose | 23 |

(17) Tablet for Endurance Enhancement or Antifatigue

Compositions (1 tablet=250 mg) described below were tableted to produce a tablet.

TABLE 24

| Nootkatone | 10% by mass |
|---|---|
| Corn starch | 50 |
| Cellulose | 10 |
| Lactose | 30 |

(18) Granule for Endurance Enhancement or Antifatigue

Compositions (1 bag=500 mg) described below were mixed to produce a granule.

TABLE 25

| Nootkatone | 1% by mass |
|---|---|
| Corn starch | 20 |
| Fructose | 30 |
| Glucose | 25 |
| Skimmed milk powder | 14 |
| Caffeine | 10 |

(19) Food for Endurance Enhancement or Antifatigue

Compositions (1 tablet=1000 mg) described below were tableted to produce a chewable tablet food.

TABLE 26

| Nootkatone | 1% by mass |
|---|---|
| Lactose | 15 |
| Maltose | 15 |
| Glucose | 20 |
| Glutamine | 10 |
| Vitamin C | 15 |
| Cellulose | 10 |
| Caffeine | 4 |

TABLE 26-continued

| Xylitol | 8 |
|---|---|
| Vitamin E | 1 |
| Flavor | 1 |

(20) Drink for Endurance Enhancement or Antifatigue

Compositions described below were mixed to produce a drink for endurance enhancement or antifatigue.

TABLE 27

| Water | 500 mL |
|---|---|
| Nootkatone | 10 mg |
| Fructose | 3 g |
| Glucose | 2 g |
| Vitamin C | 500 mg |
| Sodium citrate | 2 g |
| Malic acid | 100 mg |
| Caffeine | 50 mg |
| Flavor | Certain quantity |

(21) Capsule for Endurance Enhancement or Antifatigue

Compositions (300 mg) described below were encapsulated into an encapsulating agent.

TABLE 28

| Nootkatone | 10% by mass |
|---|---|
| Vitamin C | 20 |
| Cellulose | 10 |
| Corn starch | 45 |
| Tocopherol | 2 |
| Lactose | 13 |

The invention claimed is:

1. A method for enhancing endurance and/or for removing fatigue comprising administering to a subject in need thereof an effective amount of nootkatone in conjunction with exercise, wherein
   nootkatone is administered in an oral solid preparation comprising nootkatone in an amount ranging from 0.01 to 95% by mass,
   said oral solid preparation is selected from the group consisting of a tablet, a granule, a capsule, and
   nootkatone is selected from the group consisting of purified nootkatone, synthetic nootkatone or nootkatone extracted from grapefruit oil.

2. The method of claim 1, wherein said composition is in the form of an oral preparation comprising nootkatone in an amount ranging from 0.1 to 95% by mass.

3. The method of claim 1, wherein said oral solid preparation is a tablet.

4. The method of claim 1, wherein said composition is in the form of an oral preparation comprising nootkatone in an amount ranging from 2 to 80% by mass.

5. A method for enhancing endurance and/or for removing fatigue comprising administering to a subject in need thereof an effective amount of nootkatone, wherein
   nootkatone is administered in an oral solid preparation comprising nootkatone in an amount ranging from 0.01 to 95% by mass,
   said oral solid preparation is selected from the group consisting of a tablet, a granule, a capsule, and
   nootkatone is selected from the group consisting of purified nootkatone, synthetic nootkatone or nootkatone extracted from grapefruit oil.

6. The method of claim 5, wherein said composition is in the form of an oral preparation comprising nootkatone in an amount ranging from 0.1 to 95% by mass.

7. The method of claim 5, wherein said oral solid preparation is a tablet.

8. The method of claim 5, wherein said composition is in the form of an oral preparation comprising nootkatone in an amount ranging from 2 to 80% by mass.

9. The method of claim 1, wherein said oral solid preparation is a granule.

10. The method of claim 1, wherein said oral solid preparation is a capsule.

11. The method of claim 1, wherein said effective amount of nootkatone ranges from 1 to 2000 mg/60 kg of body weight per day.

12. The method of claim 1, wherein said effective amount of nootkatone ranges from 1 to 1000 mg/60 kg of body weight per day.

13. The method of claim 1, wherein said effective amount of nootkatone ranges from 2 to 1000 mg/60 kg of body weight per day.

14. The method of claim 1, wherein said effective amount of nootkatone ranges from 2 to 700 mg/60 kg of body weight per day.

15. The method of claim 1, wherein said effective amount of nootkatone ranges from 5 to 500 mg/60 kg of body weight per day.

16. The method of claim 5, wherein said oral solid preparation is a granule.

17. The method of claim 5, wherein said oral solid preparation is a capsule.

18. The method of claim 5, wherein said effective amount of nootkatone ranges from 1 to 2000 mg/60 kg of body weight per day.

19. The method of claim 5, wherein said effective amount of nootkatone ranges from 1 to 1000 mg/60 kg of body weight per day.

20. The method of claim 5, wherein said effective amount of nootkatone ranges from 2 to 1000 mg/60 kg of body weight per day.

21. The method of claim 5, wherein said effective amount of nootkatone ranges from 2 to 700 mg/60 kg of body weight per day.

22. The method of claim 5, wherein said effective amount of nootkatone ranges from 5 to 500 mg/60 kg of body weight per day.

* * * * *